United States Patent
Srivastava et al.

(10) Patent No.: US 6,231,832 B1
(45) Date of Patent: *May 15, 2001

(54) RADIOPHARMACEUTICAL STANNIC SN-117M CHELATE COMPOSITIONS AND METHODS OF USE

(75) Inventors: Suresh C. Srivastava, Setauket; George E. Meinken, Middle Island, both of NY (US)

(73) Assignee: Brookhaven Science Associates, Upton, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/049,640

(22) Filed: Mar. 23, 1998

(51) Int. Cl.$^7$ .............................. A61K 51/00; C07F 5/00
(52) U.S. Cl. ...................... 424/1.65; 424/1.73; 534/10
(58) Field of Search ................................ 424/1.65, 1.11, 424/1.73; 534/10, 13

(56) References Cited

U.S. PATENT DOCUMENTS

| | | | |
|---|---|---|---|
| 4,363,793 | 12/1982 | Blau et al. | 424/1.11 |
| 4,364,920 | 12/1982 | Winchell | 424/1.11 |
| 4,500,507 | 2/1985 | Wong | 424/1.11 |
| 4,533,541 | 8/1985 | Srivastava et al. | 424/1.11 |
| 4,636,380 | 1/1987 | Wong | 424/1.11 |
| 4,842,845 * | 6/1989 | Rocklage et al. | 424/1.11 |
| 4,906,450 | 3/1990 | Lieberman et al. | 424/1.11 |
| 5,276,147 | 1/1994 | Thornback et al. | 534/14 |
| 5,328,679 * | 7/1994 | Hanson et al. | 424/1.49 |
| 5,393,512 | 2/1995 | Vanderheyden et al. | 424/1.53 |
| 5,435,990 | 7/1995 | Cheng et al. | 424/1.53 |
| 5,601,800 | 2/1997 | Katti et al. | 424/1.77 |
| 5,652,361 | 7/1997 | Simon et al. | 540/474 |
| 5,853,695 * | 12/1998 | Srivastava et al. | 424/1.65 |

OTHER PUBLICATIONS

Yano et al., "Tin–117m: Production, Chemistry and Evaluation as a Bone–Scanning Agent," International Journal of Applied Radiation and Isotopes, vol. 24, pp. 319–325, 1973.*

Atkins et al., "Biodistribution of Sn–117m (4+) DTPA for Palliation Therapy of Painful Osseous Metastases," 186, Radiology, pp. 279–283, 1993.*

Oster et al., "The Development and In–Vivo Behavior of Tin Containing Radiopharmaceuticals–II. Autoradiographic and Scintigraphic Studies in Normal Animals and in Animal Models of Bone Disease," Int. J. Nucl. Med. Biol., vol. 12, No. 3, pp. 175–184 (1985).

Srivastava et al. "The Development and In–Vivo Behavior of Tin Containing Radiopharmaceuticals–I. Chemistry, Preparation, and Biodistribution in Small Animals," Int. J. Nucl. Med. Biol., vol. 12, No. 3, pp. 167–174 (1985).

Atkins et al., "Tin–117m(4+)–DTPA for Palliation of Pain from Osseous Metastases: A Pilot Study," The Journal of Nuclear Medicine, vol. 36, No. 5 (1995).

Srivastava, et al., "Treatment of Metastatic Bone Pain with Tin–117m Stannic Diethylenetriaminepentaacetic Acid: A Phase I/II Clinical Study," Clinical Cancer Research, vol. 4, pp. 61–68 (1998).

* cited by examiner

Primary Examiner—Michael G. Hartley
(74) Attorney, Agent, or Firm—Margaret C. Bogosian (57) ABSTRACT

Radiopharmaceutical compositions including $^{117m}$Sn labeled stannic ($Sn^{4+}$) chelates are provided. The chelates are preferably polyhydroxycarboxylate, such as oxalates, tartrates, citrates, malonates, gluconates, glucoheptonates and the like. Methods of making $^{117m}$Sn-labeled ($Sn^{4+}$) polyhydroxycarboxylic chelates are also provided. The foregoing pharmaceutical compositions can be used in methods of preparing bone for scintigraphical analysis, for radiopharmaceutical skeletal imaging, treatment of pain resulting from metastatic bone involvement, treatment of primary bone cancer, treatment of cancer resulting from metastatic spread to bone from other primary cancers, treatment of pain resulting from rheumatoid arthritis, treatment of bone/joint disorders and to monitor radioactively the skeletal system.

10 Claims, 5 Drawing Sheets

RADIOPHARMACEUTICAL STANNIC SN-117M CHELATE COMPOSITIONS AND METHODS OF USE

This invention was made with Government support under contract number DE-AC02-98CH10886, awarded by the U.S. Department of Energy. The Government has certain rights in the invention.

BACKGROUND OF THE INVENTION

The radiopharmaceutical reagents of this invention, a class of tin-117m radiopharmaceuticals are therapeutic agents (that also incorporate gamma-emission) that localize predominantly in bone after intravenous injection. Images reflecting bone structure or function can also be obtained by a scintillation camera that detects the distribution of ionizing radiation emitted by the radioactive tin-117m agent.

Radiochemical reagents, by virtue of their radioactive emission, have become a most useful diagnostic and therapeutic tool. Some of these reagents incorporate a gamma-emitting nuclide and localize in a specific organ or bone after intravenous injection. Images reflecting the organ or bone can then be obtained by means of a scintillation camera that detects the distribution of ionizing radiation emitted by the radioactive reagent. The principal radioactive isotope used in diagnostic procedures is technetium-99m. Other clinically important diagnostic isotopes are thallium-201, gallium-67, and iodine- 123. All the above are cyclotron-produced. Examples of therapeutic reagents which localize in pathologic tissue include iodine- 131 and phosphorus-32, both reactor-produced.

In order to be an effective radioactive drug—whether for therapeutic or diagnostic use—the reagent must combine four elements: low toxicity, specific biodistribution, low background radiation (non-target) dose, and suitable therapeutic/diagnostic radionuclidic emissions. For example, $^{99m}$technetium combines with methylene diphosphonate (MDP) to form $^{99m}$Tc-MDP, which localizes in the skeleton in general and in areas of hyperactive bone metabolism in particular. Biodistribution of this agent combines rapid, high concentration by target tissue and low uptake by surrounding tissue with rapid blood clearance and urinary excretion of the non-specifically localized radioactive drug. Thus, the amount of localized reagent to resolve the image on scintillation cameras is obtained with minimal radiation dose to the patient.

U.S. Pat. No. 4,533,541 to Srivastava, et al. discloses tin-117m radiopharmaceuticals as therapeutic and diagnostic agents that localize in bone after intravenous injection in mammals. The preferred chelates are phosphonate compounds such as pyrophosphate (PYP), methylene diphosphonate (MDP), ethylidenehydroxydisodium phosphonate (EHDP) and diethylene-triamine pentaacetic acid (DTPA).

U.S. Pat. No. 4,636,380 to Wong discloses a method of preparing nonradioactive stannous citrate for use as complexing agent for $^{111}$InCl$_3$ to form bimetallic In(Sn) citrate which when added to $^{111}$InCl$_3$ provides a covalently bonded radionuclide to a protein ligand.

Tin-117m exhibits radionuclidic properties acceptable for clinical and therapeutic use such as a half-life of 14 days, a gamma-emission of 158 keV photons, 87%, and the emission (total per decay) abundance of low energy Auger and conversion electrons. A short radioisotopic half-life is necessary to minimize patient exposure, but cannot be so short as to preclude commercial processing and transport. In addition, a useful radioisotope must yield gamma rays in reasonable abundance that can be imaged with currently available cameras. Internal scatter and absorption of low energy gamma emission and sensitivity and resolution constraints imposed by the collimators and electronics of current scintillation cameras limit useful isotopic emission from 50–60 keV to approximately 350 keV.

It has been found, however, that when using Tc-99m MDP the ratios of radioactivity concentration in bone versus other major tissues such as muscle, spleen liver, kidney and blood are high but not absolute. As a result Tc-99m will likely be found in the body in other organs in addition to sick organs.

Accordingly, it is an object of the present invention to provide radioactive chelates of tin- 117m which are easy to prepare, have chemical and biological properties superior to other bone localizing pharmaceuticals, can be used for therapy of bone cancer and other bone disorders, and have a gamma emitting component that can be used for imaging biodistribution and for calculating dosimetry prior to initiating high-dose therapeutic administrations. It is another object of the present invention to provide therapeutic radiopharmaceuticals which have high bone uptake and as a result localize almost exclusively in skeletal tissue and exhibit low accumulation in other organs.

SUMMARY OF THE INVENTION

The present invention, which addresses the needs of the prior art, provides radiopharmaceutical compositions which includes $^{117m}$Sn labeled stannic (Sn$^{4+}$) chelates. The chelates are polyhydroxycarboxylates selected from the group consisting of oxalates, tartrates, citrates, malonates, gluconates, glucoheptonates and the like. Mixtures of the foregoing polyhydroxycarboxylates are also contemplated.

The present invention also provides a method of making $^{117m}$Sn labeled stannic (Sn$^{4+}$) polyhydroxycarboxylate. The method includes reacting $^{117m}$SnCl$_2$ with a polyhydroxycarboxyclic acid followed by oxidizing the product of the first step with an oxidizing agent. Useful oxidizing agents include hydrogen peroxide and others that are compatible with the physiological system. An effective amount of tin-117m stannic polycarboxylate can be administered to localize in bone for scintigraphical analysis. The invention thus provides a method for radiopharmaceutical skeletal imaging which includes administering intravenously tin-117m labeled stannic polycarboxylate and detecting the radioactivity by applicable detection techniques. Methods for treatment of pain resulting from metastatic bone involvement including administering an effective amount of tin-117m labeled stannic polycarboxylate to a mammal are also provided by this invention. In this specification, bone involvement refers to the metastatic spread of cancer to bone. This invention also provides a method of treatment of primary bone cancer, which contemplates administering an effective amount of tin-117m stannic (Sn4+) polycarboxylate to a mammal. The pharmaceutical compositions of the present invention can also be used in a method for treatment of cancer in bone, wherein the cancer results from metastatic spread to bone from other primary cancers. Similarly, the radiopharmaceutical compositions of the present invention can also be used in a method for treatment of bone/joint disorders, such as osteoporosis, Paget's disease, rheumatoid arthritis, osteoarthritis and the like, which includes administering an effective amount of the radiopharmaceutical composition of the present invention to a mammal. Additionally, the radiopharmaceutical composition of the present invention is also useful in a method of monitoring a skeletal system which includes administering a detectable amount of $^{117m}$Sn labeled stannic (Sn$^{4+}$) polycarboxylate and measuring the distribution of radioactivity throughout bony tissue and other parts of the body by applicable detection techniques.

As a result of the present invention, tin-117m stannic chelates of polyhydroxy-carboxylic acids (citrate is an example) are provided which localize almost exclusively in bone and clear rapidly from blood and other organs. Moreover, the ligands used to form tin-117m chelates provide pharmaceuticals with reduced in vivo chemical toxicity than previously developed ligands such as DTPA, PYP, MDP and EHDP.

Other improvements which the present invention provides over the prior art will be identified as a result of the following description which sets forth the preferred embodiments of the present invention. The description is not in any way intended to limit the scope of the present invention, but rather only to provide working examples of the present preferred embodiments. The scope of the present invention will be pointed out in the appended claims.

DETAILED DESCRIPTION OF THE INVENTION

Tin-117m was produced by the $^{117m}$Sn $(n,n^1,\gamma)^{117m}$Sn reaction in the High Flux Beam Reactor (HFBR) at Brookhaven National Laboratory (BNL) or at the High Flux Isotope Reactor (HFIR) at Oak Ridge National Laboratory (ORNL), with a specific activity of 2mCi/mg to 10mCi/mg as the metal. Higher or lower specific activities will also produce stable chelates. $^{117m}$Sn has a half life of 14.0 days, Auger and conversion electrons in good abundance (110%) and a 159 KeV photon (86.4% abundance). The abundance of conversion electrons is calculated based on the sum of the abundance of five conversion electrons, namely CE-Ki having an energy of 126.8 KeV and an abundance of 64.8 CE-K2 having an energy of 129.4 KeV and an abundance of 11.7%, CE-Li having an energy of 151.6 KeV and an abundance of 26.1%, CE-L2 having an energy of 154.1 KeV and an abundance of 1.5% and CE-M1 having an energy of 155.1 KeV and an abundance of 5.6%.

The metal was dissolved in a minimum quantity of concentrated HCl in an inert atmosphere and diluted with water to give a stannous chloride solution in 1–4N HCl as desired. A stable chelate was formed when excess ligand was added to this tin solution. More specifically, the ligand to tin ratio must be higher than 1:1, and preferably 20:1. pH was adjusted with NaOH to from about 3 to about 8. The preferred ligands are all from the class of polyhydroxycarboxylic acids, for example, oxalate, tartrate, citrate, malonate, gluconate, and glucoheptonate and the like. Of these ligands, citrate is most preferred.

Aliquots of these solutions were oxidized to stannic complexes by the addition of $H_2O_2$ in a two-to ten-fold molar excess over tin. Radiochemical purity and the oxidation state of tin were checked by various in-vitro methods including paper chromatography, gel filtration, and HPLC. Tissue distribution studies were done in normal laboratory mice (BNL or others). All animals were injected with the appropriate radiopharmaceutical intravenously. A number of time periods up to 30 days after injection were used to collect the data.

As used herein, radiopharmaceuticals include radiochemicals and radioactive drugs and reagents as tested on animals. These reagents exhibit characteristics similar to other known radiopharmaceuticals such as those derived from technetium-99m and iodine-131.

Comparative studies were conducted using tin-117m stannic citrate, tin-117m stannic DTPA and Tc-99m MDP. The tissue biodistribution of tin-117m stannic citrate was significantly better than the commonly used bone scanning agent, Tc-99m MDP as shown in Table 3 and in FIG. 3. Tin-117m stannic citrate localized in the bone and cleared rapidly from other tissues. As a result of these findings, Sn 117m citrate, as well as stannic chelates with other hydroxycarboxylic acids, e.g., oxalate, tartrate, malonate, gluconate, and glucoheptonate, etc. make very effective radiopharmaceuticals for treatment of metastatic bone pain, of primary bone cancer and for radiotherapy of other disorders of bone and of other organs.

A comparison of the toxicity profiles of citrate and DTPA from the literature would indicate that tin-117m stannic citrate will have much less in-vivo toxicity than the previously used ligands including DTPA.

Due to reduced chemical toxicity, Sn-117m citrate can be prepared using Sn-117m of a wide range of specific activities, thus allowing the use of more commonly available low flux reactors such as the reactor at the University of Missouri, Columbia, Mo. (MURR), and others.

EXAMPLES

The following examples serve to provide further appreciation of the invention. The materials used in the examples have been synthesized as described above (e.g., tin-117m stannic citrate or stannic DTPA) or are commercially readily available (Tc-99m MDP). In mouse biodistribution experiments, only selected tissues are shown in the examples below. These tissues were collected from a total of ten organ samples, namely, blood, spleen, stomach, intestine, liver, kidneys, heart, lung, muscle, and bone.

Example 1

Figure 1:
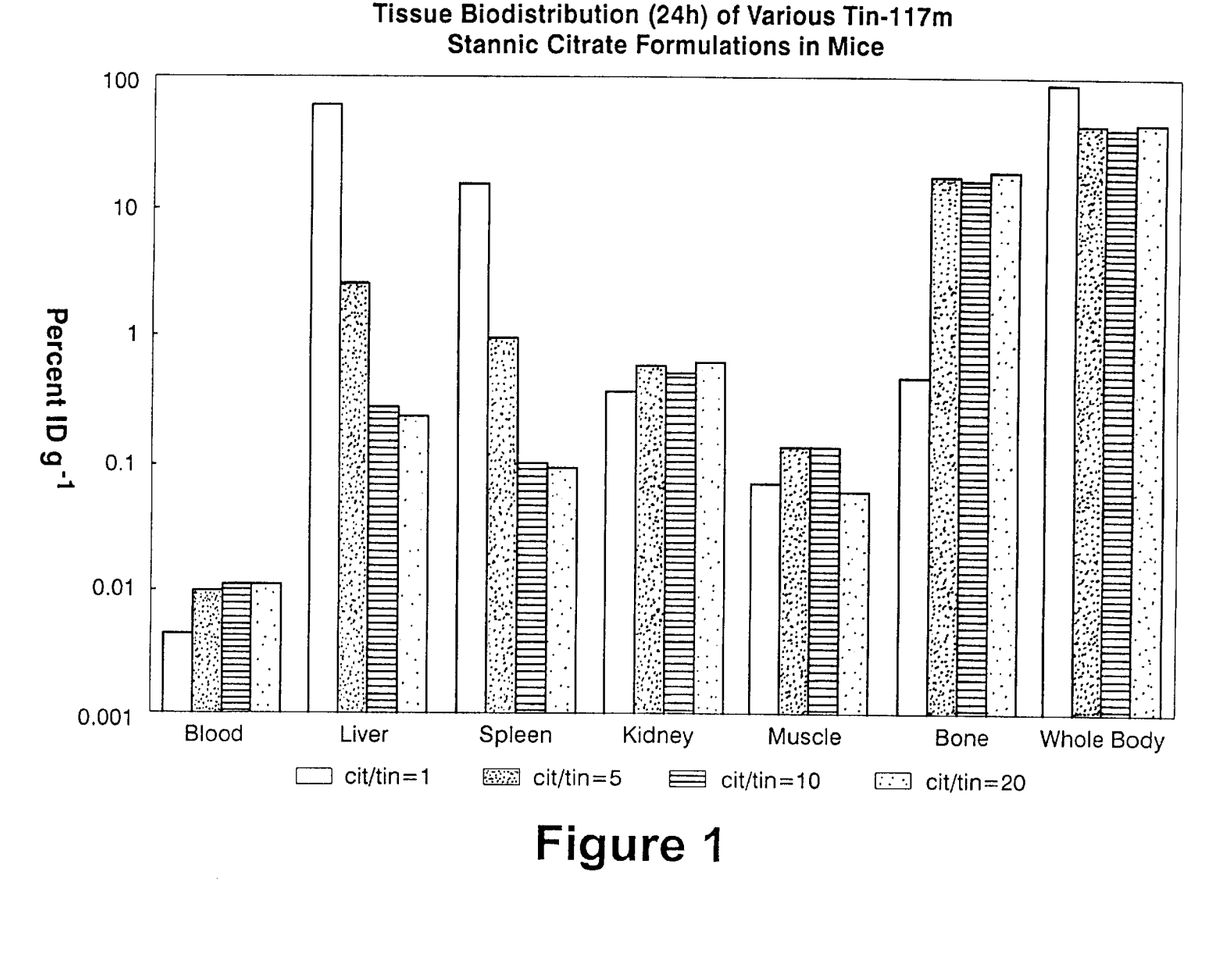
FIG. 1 is a block diagram showing tissue biodistribution expressed as % injected dose per gram after 24 hours of various tin-117m citrate formulations in mice.
Figure 4:
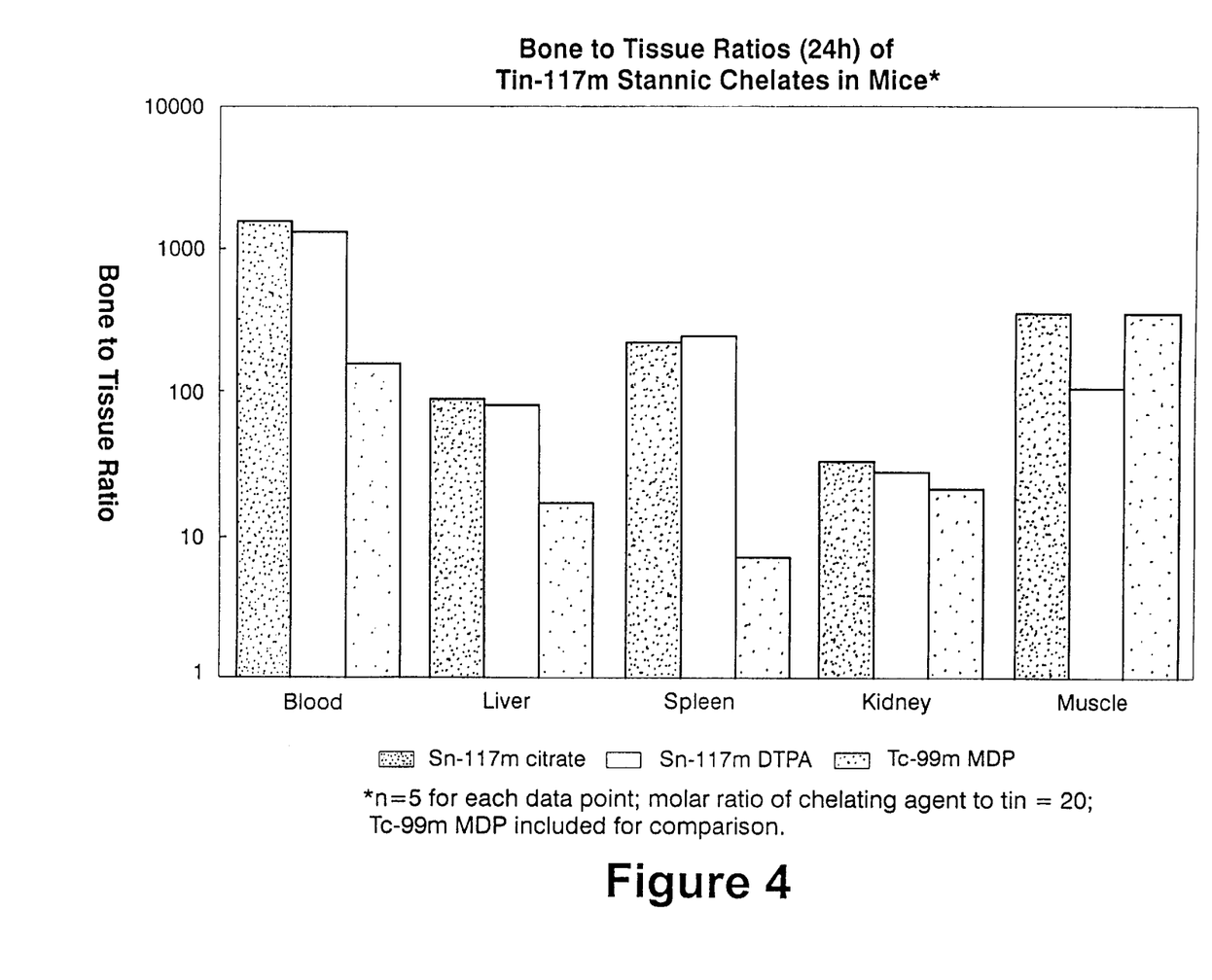
FIG. 4 is a block diagram illustrating bone to tissue ratios after 24 hours of tin-117m stannic chelates in mice. The molar ratio of chelating agent to tin is 20 Tc-99m MDP is included for comparison.

Tin-117m stannic citrate formulations prepared using varying citrate to tin molar ratios were administered intravenously into mice. Table 1 below and FIG. 1 herein show the tissue biodistribution after 24 hours of various tin-117m stannic citrate formulations used in this example.

apparent that tissue biodistribution of tin-117m stannic citrate was significantly better than the commonly used bone scanning agent Tc-99m MDP and comparable to that of tin-117m stannic DTPA. Ratios of uptake into bone versus other tissues based on values in Table 2 are set forth in Table 3 below, and plotted as a block diagram in FIG. 4 herein.

TABLE 1

TISSUE BIODISTRIBUTION (24H) OF VARIOUS TIN-117m STANNIC CITRATE FORMULATIONS IN MICE*

| Citrate to tin molar ratio | Blood | Spleen | Stomach | Intestine | Liver | Kidney | Heart | Lungs | Muscle | Bone | Whole body, % ID |
|---|---|---|---|---|---|---|---|---|---|---|---|
| 1 | 0.004 ± 0.001 (113) | 14.61 ± 3.1 (0.03) | 0.039 ± 0.05 (12) | 0.019 ± 0.006 (24) | 63.68 ± 2.3 (0.007) | 0.339 ± 0.113 (1) | 0.557 ± 0.88 (0.8) | 0.375 ± 0.156 (1) | 0.065 ± 0.034 (7) | 0.45 ± 0.669 | 95.2 ± 1.64 |
| 5 | 0.009 ± 0.003 (1958) | 0.875 ± 0.035 (20) | 0.074 ± 0.045 (243) | 0.071 ± 0.035 (249) | 2.38 ± 0.198 (7) | 0.537 ± 0.158 (33) | 0.030 ± 0.005 (195) | 0.091 ± 0.023 (590) | 0.126 ± 0.078 (141) | 17.72 ± 1.85 | 46.2 ± 2.3 |
| 10 | 0.010 ± 0.003 (1660) | 0.094 ± 0.016 (177) | 0.042 ± 0.008 (405) | 0.041 ± 0.009 (415) | 0.256 ± 0.032 (65) | 0.481 ± 0.096 (35) | 0.030 ± 0.006 (553) | 0.085 ± 0.017 (195) | 0.127 ± 0.087 (132) | 16.6 ± 1.17 | 43.2 ± 4.1 |
| 20 | 0.012 ± 0.004 (1595) | 0.087 ± 0.008 (230) | 0.052 0.013 (388) | 0.045 ± 0.018 (440) | 0.214 ± 0.032 (92) | 0.593 ± 0.049 (33) | 0.037 ± 0.007 (535) | 0.107 ± 0.018 (187) | 0.057 ± 0.056 (347) | 19.78 1.65 | 47.3 ± 2.4 |

*% Injected dose (ID) per g; n = 5 for each data point; bone to tissue ratios in parentheses.

Figure 2:
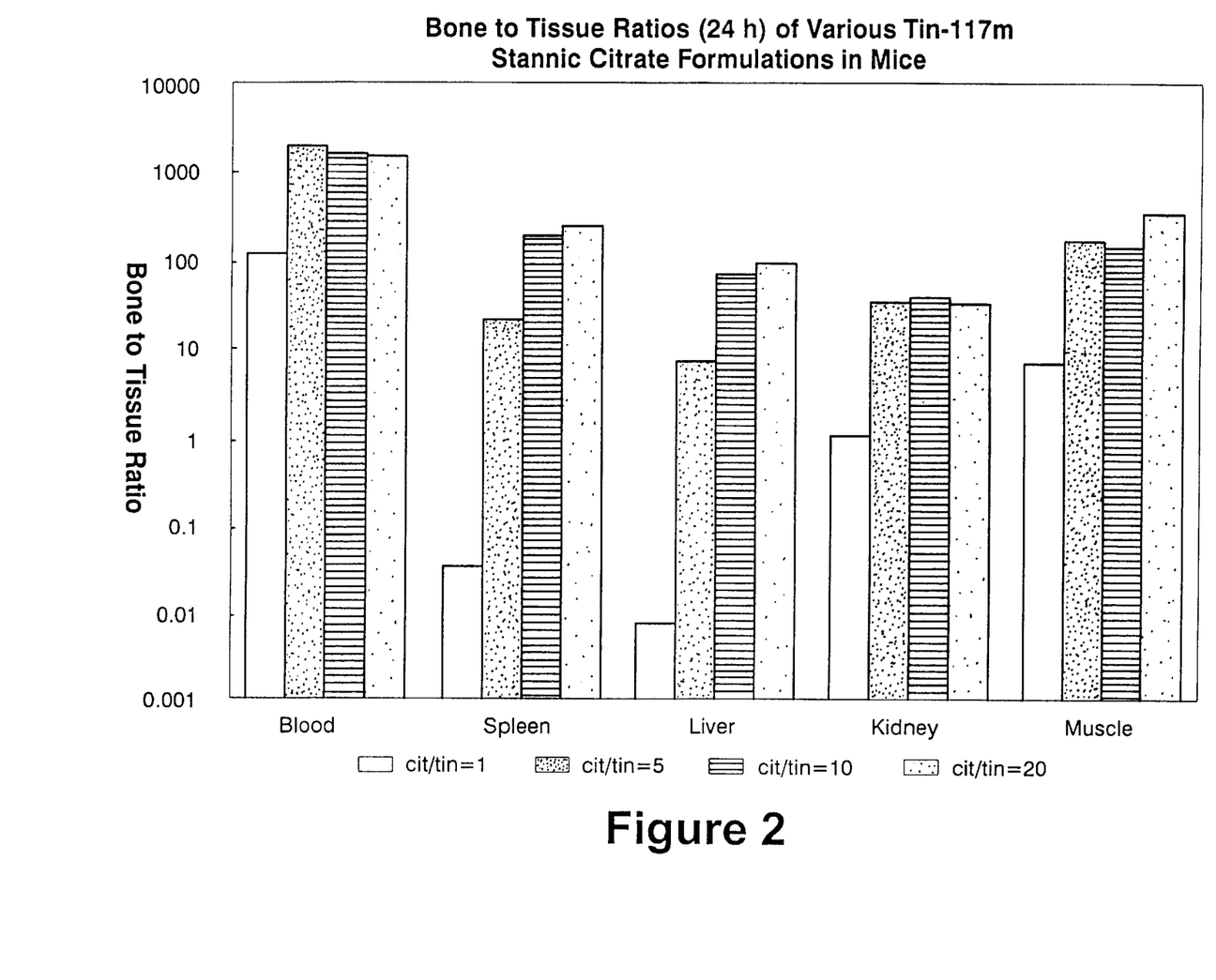
FIG. 2 is a block diagram illustrating bone to tissue ratios after 24 hours of various tin-117m stannic citrate formulations in mice.

As shown in Table 1 above, formulations having citrate to tin molar ratios of 1:1, 5:1, 10:1 and 20:1 were used. Based on the tissue uptake values obtained for various organs tested, at a citrate:tin molar ratio greater than 5:1, tin-117m stannic citrate localized almost exclusively in bone and cleared rapidly from blood and other organs. At molar ratios of citrate to tin of 1:1 and 5:1, soft tissue uptake was higher. FIG. 2 herein shows the bone to tissue ratios after 24 hours of various tin-117m stannic citrate formulations in mice as set forth in Table 1.

Example 2

A comparative study was conducted using tin-117m stannic citrate (citrate:tin ratio of 20:1), tin-117m stannic DTPA (DTPA to tin molar ratio of 20:1) and Tc-99m MDP. Tissue biodistribution after 24 hours was measured in bone and other major tissues as set forth in Table 2 below.

TABLE 2

TISSUE BIODISTRIBUTION (24H) OF TIN-117m STANNIC CHELATES IN MICE*

| Preparation | Blood | Spleen | Stomach | Intestine | Liver | Kidney | Heart | Lungs | Muscle | Bone | Whole body, % ID |
|---|---|---|---|---|---|---|---|---|---|---|---|
| Tin-117m (4+) citrate | 0.012 ± 0.004 | 0.087 ± 0.008 | 0.052 ± 0.013 | 0.045 ± 0.018 | 0.214 ± 0.032 | 0.593 ± 0.049 | 0.037 ± 0.007 | 0.107 ± 0.018 | 0.057 ± 0.056 | 19.78 ± 1.65 | 47.3 ± 2.4 |
| Tin-117m (4+) DTPA | 0.014 ± 0.003 | 0.076 ± 0.006 | 0.045 ± 0.013 | 0.047 ± 0.009 | 0.22 ± 0.015 | 0.651 ± 0.032 | 0.042 ± 0.006 | 0.115 ± 0.019 | 0.169 ± 0.177 | 18.39 ± 0.45 | 47.44 ± 1.8 |
| Tc-99m MDP** | 0.07 ± 0.04 | 1.59 ± 1.41 | 0.10 ± 0.04 | 0.09 ± 0.08 | 0.62 ± 0.25 | 0.52 ± 0.14 | 0.05 ± 0.02 | — | 0.03 ± 0.01 | 11.01 ± 1.67 | 23.61 ± 2.53 |

Figure 3:
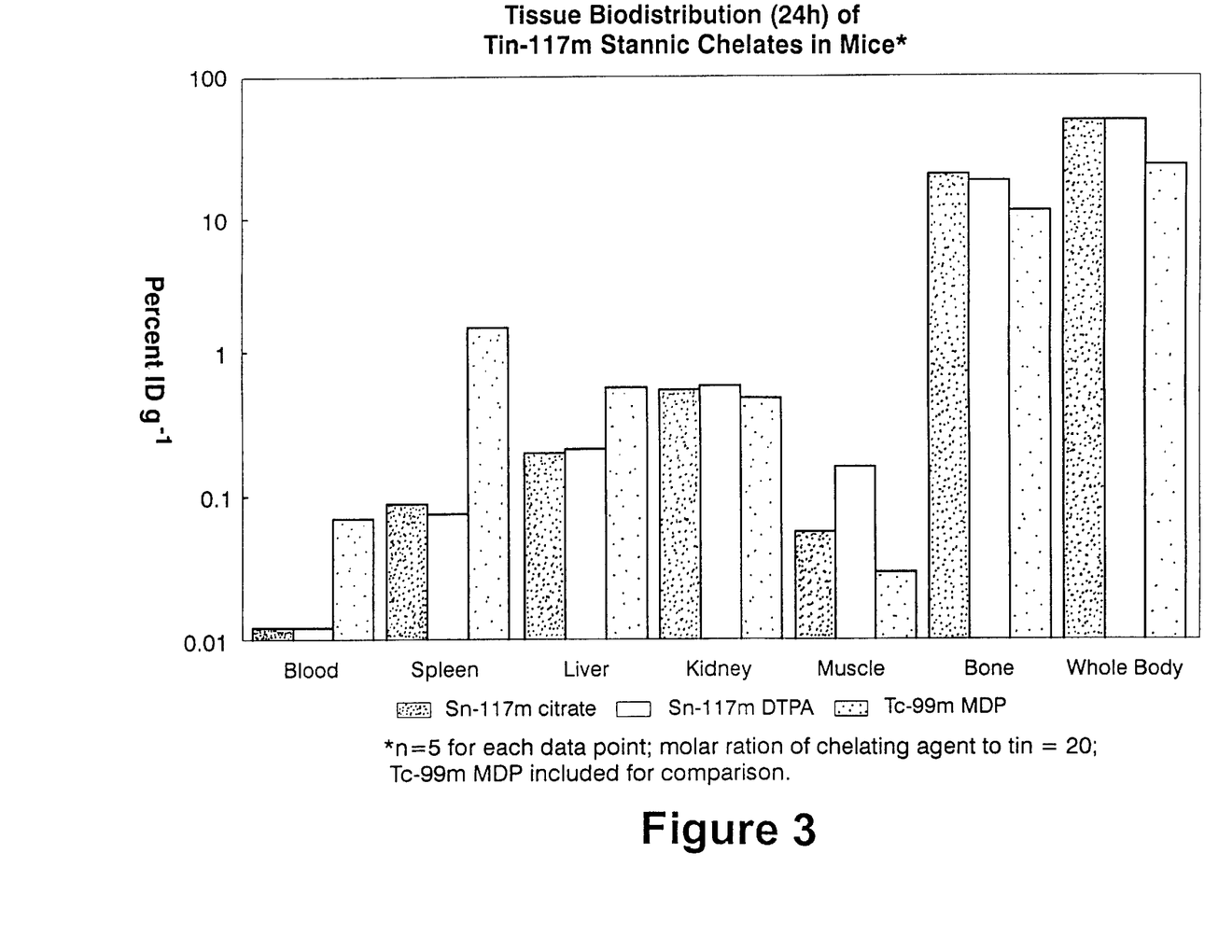
FIG. 3 is a block diagram showing tissue biodistribution expressed as % injected dose per gram after 24 hours of tin-117m stannic chelates in mice. The molar ratio of chelating agent to tin is 20. Tc-99m MDP is included for comparison.

\* % Injected dose (ID) per g; n = 5 for each data point; molar ratio of chelating agent to tin = 20
\*\* Routinely used bone scanning agent; included for comparison FIG. 3 herein is a block diagram of the information contained in Table 2. From Table 2 and FIG. 3, it is readily

TABLE 3

BIODISTRIBUTION DATA (24H) OF TIN-117M STANNIC CHELATES IN MICE*

| Preparation | % Injected dose | | Ratio Bone to | | | | | | | | |
|---|---|---|---|---|---|---|---|---|---|---|---|
| | Bone ($g^{-1}$) | Whole body | Blood | Spleen | Stomach | Intestine | Liver | Kidney | Heart | Lungs | Muscle |
| Tin-117m (4+) citrate | 19.78 ± 1.65 | 47.3 ± 2.4 | 1595 | 230 | 388 | 440 | 92 | 33 | 535 | 187 | 347 |
| Tin-117m (4+) DTPA | 18.39 ± 0.45 | 47.44 ± 1.8 | 1352 | 242 | 411 | 393 | 84 | 28 | 449 | 160 | 109 |
| Tc-99m MDP** | 11.01 ± 1.67 | 23.61 ± 2.53 | 157 | 7 | 110 | 122 | 18 | 21 | 220 | — | 367 |

\* n = 5 for each data point; molar ratio of chelating agent to tin = 20
\*\* Routinely used bone scanning agent; included for comparison Example 3

Figure 5:
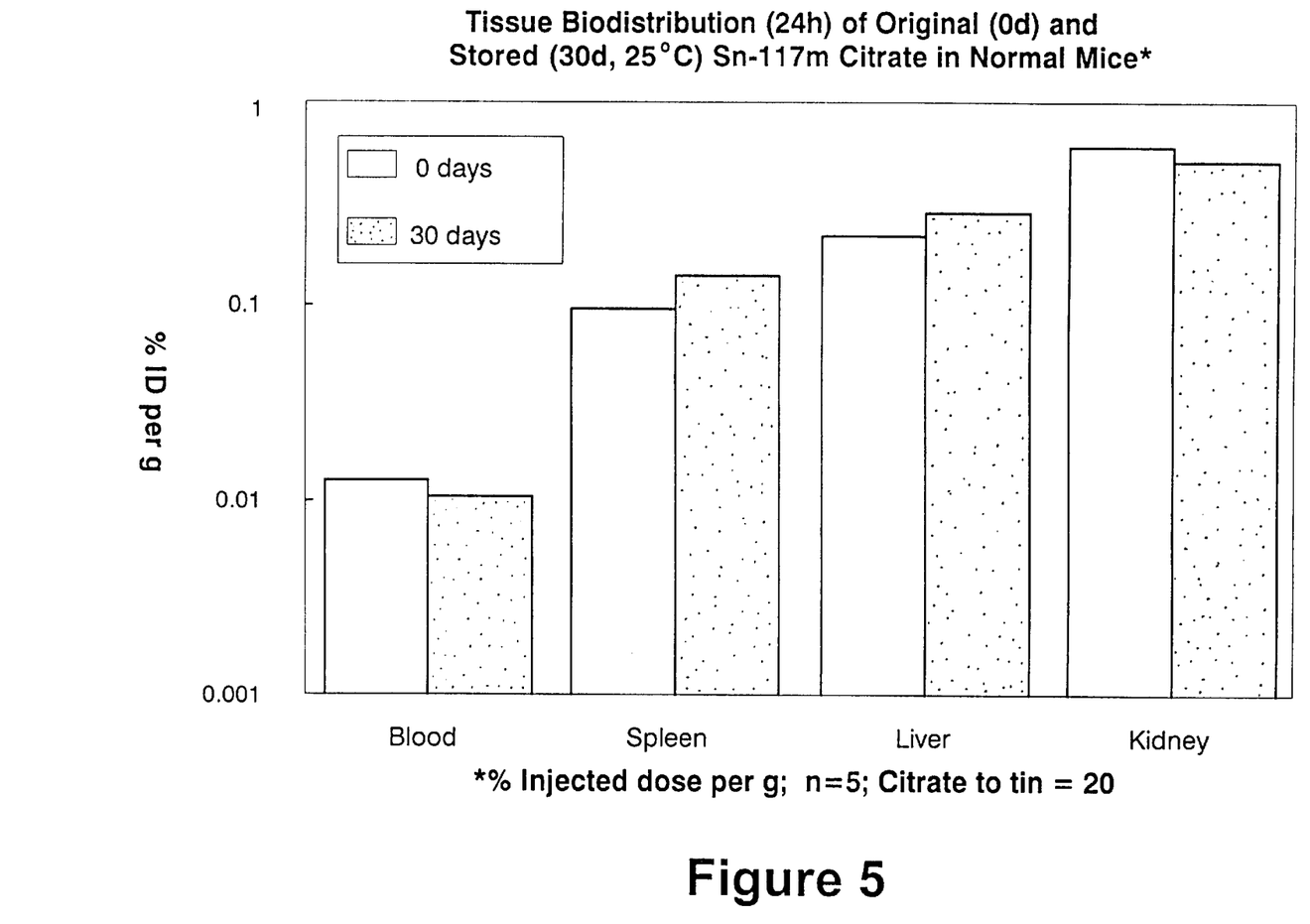
FIG. 5 is a block diagram showing tissue biodistribution expressed as % injected dose per gram after 24 hours of original (0 day) and stored (30 day, 25° C.) Sn-117m stannic citrate in mice.

In this example, tissue biodistribution of fresh tin-117m stannic citrate and of tin-117m stannic citrate stored at least 30 days at room temperature (25° C.) were studied in mice. The results are set forth in Table 4 below and are also plotted as a block diagram in FIG. 5 herein.

TABLE 4

TISSUE BIODISTRIBUTION OF FRESH (0d) AND STORED (30d, 25° C.) Sn-117m STANNIC CITRATE IN MICE*

| Preparation | Blood | Spleen | Stomach | Intestine | Liver | Kidney | Heart | Lungs | Muscle | Bone | Whole body, % ID |
|---|---|---|---|---|---|---|---|---|---|---|---|
| 0 day | 0.012 ± 0.004 (1595) | 0.087 ± 0.008 (230) | 0.052 ± 0.013 (388) | 0.045 ± 0.018 (440) | 0.214 ± 0.032 (92) | 0.593 ± 0.049 (33) | 0.037 ± 0.007 (535) | 0.107 ± 0.018 (187) | 0.057 ± 0.056 (347) | 19.78 ± 1.65 | 47.3 ± 2.4 |
| 30 day | 0.01 ± 0.003 (1295) | 0.128 ± 0.03 (112) | 0.035 ± 0.008 (407) | 0.038 ± 0.005 (385) | 0.272 ± 0.042 (52) | 0.494 ± 0.029 (29) | 0.033 ± 0.005 (432) | 0.129 ± 0.25 (111) | 0.075 ± 0.06 (190) | 14.26 ± 1.42 | 36 ± 2.49 |

\* % ID per g at 24h; r = 5 for each data point; bone to tissue ratio in parentheses; molar ratio citrate: tin = 20:1.

From Table 4 above, it can be seen that tin-117m stannic citrate was stable at room temperature (25° C.) for at least 30 days, providing a tissue biodistribution in mice which is essentially unaltered after 30 days storage.

What is claimed is:

1. A radiopharmaceutical composition consisting essentially of $^{117m}$Sn labeled stannic ($Sn^{4+}$) chelate, wherein said chelate is a polyhydroxycarboxylate selected from the group consisting of oxalate, malonate, gluconate, glucoheptonate and mixtures thereof.

2. A method of making $^{117m}$Sn labeled stannic ($Sn^{4+}$) polyhydroxycarboxylate chelates consisting essentially of:

(i) reacting $^{117m}$Sn $Cl_2$ with a polyhydroxycarboxylic acid selected from the group consisting of oxalic acid, malonic acid, gluconic acid, glucoheptonic acid and mixtures thereof; and (ii) oxidizing the product of step (i) with an oxidizing agent.

3. A method of preparing bone for scintigraphical analysis consisting essentially of administering a scintigraphically effective amount of tin-117m stannic polycarboxylate, wherein said polycarboxylate is selected from the group consisting of oxalate, malonate, gluconate, glucoheptonate and mixtures thereof.

4. A method for radiopharmaceutical skeletal imaging consisting essentially of administering intravenously tin-117m labeled ($Sn^{4+}$) polycarboxylate and detecting the radioactivity by applicable detection techniques, wherein said polycarboxylate is selected from the group consisting of oxalate, malonate, gluconate, glucoheptonate and mixtures thereof.

5. A method for treatment of pain resulting from metastatic bone involvement, consisting essentially of administering an effective amount of $^{117m}$Sn-labeled stannic (4+) polycarboxylate to a mammal, wherein said polycarboxylate is selected from the group consisting of oxalate, malonate, gluconate, glucoheptonate and mixtures thereof.

6. A method for treatment of primary bone cancer consisting essentially of administering an effective amount of $^{117m}$Sn-labeled stannic (4+) polycarboxylate to a mammal, wherein said polycarboxylate is selected from the group consisting of oxalate, malonate, gluconate, glucoheptonate and mixtures thereof.

7. A method for treatment of cancer in bone, resulting from metastatic spread to bone from other primary cancers, consisting essentially of administering an effective amount of $^{117m}$Sn-labeled stannic (4+) polycarboxylate to a mammal, wherein said polycarboxylate is selected from the group consisting of oxalate, malonate, gluconate, glucoheptonate and mixtures thereof.

8. A method for treatment of bone/joint disorders consisting essentially of administering an effective amount of $^{117m}$Sn-labeled stannic (4+) polycarboxylate to a mammal, wherein said polycarboxylate is selected from the group consisting of oxalate, malonate, gluconate, glucoheptonate and mixtures thereof.

9. A method of monitoring a skeletal system consisting essentially of administering a detectable amount of $^{117m}$Sn-labeled stannic (Sn$^{4+}$) polycarboxylate and measuring the distribution of radioactivity throughout the body by applicable detection techniques, wherein said polycarboxylate is selected from the group consisting of oxalate, malonate, gluconate, glucoheptonate and mixtures thereof.

10. A method according to claim 8, wherein said bone/joint disorder is selected from the group consisting of osteoporosis, Paget's Disease, rheumatoid arthritis and osteoarthritis.

* * * * *